US008580546B2

(12) United States Patent
Gonda et al.

(10) Patent No.: US 8,580,546 B2
(45) Date of Patent: Nov. 12, 2013

(54) MICRO-ORGAN DEVICE (71) Applicants: United States of America as represented by the Administrator of the National Aeronautics and Space Administration, Washington, DC (US); Iris Von Gustedt-Gonda, Highlands Ranch, CO (US)

(72) Inventors: Steve R. Gonda, Houston, TX (US); Robert C. Chang, Philadelphia, PA (US); Binil Starly, Norman, OK (US); Christopher Culbertson, Saint George, KS (US); Heidi L. Holtorf, Nederland, TX (US); Wei Sun, Cherry Hill, NJ (US); Julia Leslie, Houston, TX (US)

(73) Assignee: The United States of America as represented by the Administrator of the National Aeronautics and Space Administration, Washington, DC (US)

( * ) Notice: Subject to any disclaimer, the term of this patent is extended or adjusted under 35 U.S.C. 154(b) by 0 days.

(21) Appl. No.: 13/688,982

(22) Filed: Nov. 29, 2012

(65) Prior Publication Data
US 2013/0109594 A1 May 2, 2013

Related U.S. Application Data (62) Division of application No. 12/058,227, filed on Mar. 28, 2008, now Pat. No. 8,343,740.

(60) Provisional application No. 60/908,918, filed on Mar. 29, 2007.

(51) Int. Cl.
C12N 11/00 (2006.01)
C12N 11/16 (2006.01)
C12N 9/00 (2006.01)
C12N 9/99 (2006.01)
C12P 21/04 (2006.01)

(52) U.S. Cl.
USPC ...... 435/174; 435/70.3; 435/283.1; 435/284.1

(58) Field of Classification Search
None
See application file for complete search history.

(56) References Cited

U.S. PATENT DOCUMENTS 5,888,720 A * 3/1999 Mitrani ............................ 435/1.1
6,197,575 B1 * 3/2001 Griffith et al. ............... 435/288.4
6,372,482 B1 * 4/2002 Mitrani ........................ 435/284.1

OTHER PUBLICATIONS

Yan et al., Biomaterials, vol. 26, Issue 29, Oct. 2005, pp. 5864-5871.*

* cited by examiner

Primary Examiner — Chris R Tate
Assistant Examiner — Douglas F White
(74) Attorney, Agent, or Firm — Kurt G. Hammerle (57) ABSTRACT

A method for fabricating a micro-organ device comprises providing a microscale support having one or more microfluidic channels and one or more micro-chambers for housing a micro-organ and printing a micro-organ on the microscale support using a cell suspension in a syringe controlled by a computer-aided tissue engineering system, wherein the cell suspension comprises cells suspended in a solution containing a material that functions as a three-dimensional scaffold. The printing is performed with the computer-aided tissue engineering system according to a particular pattern. The micro-organ device comprises at least one micro-chamber each housing a micro-organ; and at least one microfluidic channel connected to the micro-chamber, wherein the micro-organ comprises cells arranged in a configuration that includes microscale spacing between portions of the cells to facilitate diffusion exchange between the cells and a medium supplied from the at least one microfluidic channel.

5 Claims, 8 Drawing Sheets

MICRO-ORGAN DEVICE

CROSS REFERENCE TO RELATED APPLICATIONS

This is a divisional application of application Ser. No. 12/058,227 filed on Mar. 28, 2008, which claims the benefit of U.S. Provisional Application Ser. No. 60/908,918, filed on Mar. 29, 2007.

ORIGIN OF INVENTION

The invention described herein was made in the performance of work under a NASA contract and is subject to Public Law 96-517 (35 U.S.C. §200 et seq.). The contractor has not elected to retain title to the invention. The invention described herein was also made by employee(s) of the United States Government and may be manufactured and used by or for the Government of the United States of America for governmental purposes without the payment of any royalties thereon or therefor.

BACKGROUND OF INVENTION

1. Field of Invention

The invention relates generally to devices for testing of biologics. More particularly, this invention relates to micro-organ devices and methods for fabricating and using such devices.

2. Discussion of the Related Art

Testing of pharmaceuticals and biological compounds in humans or in animals is not always possible, at least not in the early stage. Moreover, while in vivo animal studies can provide data more relevant to human responses, animal tests are expensive, labor-intensive, and time consuming. Accordingly, sometimes decisions need to be made based on in vitro data. However, extrapolating in vitro data (e.g., cell culture data) to the in vivo relevant conditions is often difficult. Although pharmacokinetic principles can be used to derive some conclusions, this approach has limitations due to various reasons.

For example, cell cultures under traditional assay conditions may not function in the same ways as cells would in natural settings because the communication and interactions between different tissues and organs are absent. In culture, cells are typically grown at the bottom of chambers or wells. These systems may have unrealistically high liquid-to-cell ratios. Even if the cells are grown on microcarrier beads, which more closely resemble physiological conditions, they still may not mimic physiological conditions accurately enough to provide reliable data.

Additionally, while controlling the spatial orientation of cells having a cell-cell interaction in a co-culture would improve traditional cell culture methods, the cell-cell interactions between different cell types do not always allow proper interactions between different cell types. In humans and animals, the liver plays an important role in the metabolism and bioavailability of pharmaceuticals and biological compounds. Consequently, methods of predicting human response from in vitro cell culture assays are complicated, and systems or devices of the related art designed to replicate in vivo organs or systems of humans or animals have not performed quite as predicted.

Accordingly, scientists with ordinary skill in the art related to this subject matter have recognized a long-felt need for in vitro organ or system models that can mimic the in vivo organs or systems in humans or animals. The related art includes U.S. Pat. No. 5,612,188 issued to Shuler et al., which is hereby incorporated by reference. This patent discloses a multi-compartmental cell culture system comprising culture chambers, sensors, and pumps, but is a system operating on a large scale, so the physiological parameters vary considerably from those found in an in vivo situation.

The related art also includes U.S. Pat. No. 7,288,405 by Shuler et al., which is incorporated herein by reference. This reference discloses in vitro microscale cell culture analog devices that permit cells to be maintained in vitro under conditions similar to those found in vivo. The microscale culture device comprises a fluidic network of channels segregated into discrete but interconnected chambers. The specific chamber geometry is designed to provide cellular interactions, liquid flow, and liquid residence parameters that correlate with those found for the corresponding cells, tissues, or organs in vivo. Fluidics are designed to accurately represent primary elements of the circulatory or lymphatic systems. In one embodiment, the components are integrated into a chip format. The design and validation of these geometries is based on a physiological-based pharmacokinetic (PBPK) model, a mathematical model that represents the body as interconnected compartments representing different tissues.

Similarly, U.S. Patent Application Publication No. 2003/0152909 A1 discloses micro-organ cultures which include isolated populations of cells having specific characteristics. These micro-organ cultures have the ability to be maintained in culture for relatively long periods of time, as well as the preservation of an organ micro-architecture which facilitates, for example, cell-cell and cell-matrix interactions analogous to those in the source organ.

These organ models of the related art demonstrate the advantages of in vitro systems for pharmaceutical or biological compounds testing. However, the related art approaches rely on directly placing the cells in the chamber or seeding the cells and allowing them to grow in the chamber. These approaches do not always provide reproducible organs. Therefore, there remains a need for in vitro organ devices, and methods for their preparation, which can mimic the in viva organs or systems in humans and animals.

SUMMARY OF INVENTION

In one aspect, embodiments of the present invention relate to methods for fabricating a micro-organ device. In accordance with one embodiment, the method for fabricating includes providing a microscale support having one or more microfluidic channels and one or more micro-chambers for housing a micro-organ and printing a micro-organ on the microscale support using a cell suspension in a syringe controlled by a computer-aided tissue engineering system, wherein the cell suspension comprises cells suspended in a solution containing a material that functions as a scaffold, and wherein the printing is performed with the computer-aided tissue engineering system according to a pattern.

In another aspect, embodiments of the present invention relate to micro-organ devices. A micro-organ device in accordance with one embodiment includes at least one micro-chamber each housing a micro-organ; and at least one microfluidic channel connected to the micro-chamber, wherein the micro-organ comprises cells arranged in a configuration that includes microscale spacing between portions of the cells to facilitate diffusion exchange between the cells and a medium supplied from the at least one microfluidic channel.

Other aspects and advantages of the embodiments described herein will become apparent from the following

DETAILED DESCRIPTION OF EXEMPLARY EMBODIMENTS

Exemplary embodiments of the invention will now be described with reference to the accompanying figures. Like elements or components in the figures are denoted with the same reference characters for consistency.

Before beginning a detailed description of some exemplary embodiments of the invention, the meaning of certain terms as used herein will be given.

"Bioprint" or "bioprinting", as used in this description, refers to a process of depositing biological materials, such as, for example, forming micro-organs using a computer-aided tissue engineering (CATE) system to print a micro-organ according to a particular design or pattern. These processes will be described in more detail below.

"Microscale" as used herein refers to dimensions no greater than 10 cm, preferably no greater than 1 cm.

"Microchip" as used herein refers to a microscale support having one or more microfluidic channels and one or more micro-chambers for housing micro-organs. A microchip typically has a dimension on the order of a few centimeters.

"Microfluidic channel" as used herein refers to a channel on a microchip. Such channels typically have depth and width that are less than a few millimeters, preferably less than 1 mm.

"Micro-chamber" as used herein refers to a structure (e.g., a well or indentation) on a microchip. A micro-chamber typically has a dimension of no greater than a few cm, preferably 1 cm or less. A micro-chamber is typically used for housing cells of a micro-organ.

"Micro-organ" as used herein refers to cells or tissue bioprinted on a microchip, typically in a micro-chamber on the microchip.

"Micro-organ device" or "MOD" as used herein refers to a device having at least one micro-organ on a support (such as a microchip).

Embodiments of the invention relate to methods for producing or fabricating micro-organ devices (MODs) using a bioprinting system for forming cells encapsulated in a structure and to the micro-organ devices thus produced. The micro-organ devices in accordance with the embodiments described herein comprise microscale three-dimensional (3D) tissue analogs in devices that include microfluidic channels and chambers.

In accordance with embodiments of the invention, different mammalian tissues may be mimicked on such micro-organ devices for various applications, such as experimental pharmaceutical screening for efficacy, adsorption, distribution, metabolism, elimination, and toxicity. Thus, these devices may be used to assess the beneficial and detrimental effects of a novel drug after it passes through a given metabolic pathway. For example, the therapeutic or toxic effects of a drug on any cell type in vitro may be assessed in the presence of microencapsulated liver cells to take into account the liver-dependent metabolic modifications of the candidate drug. In addition, these devices may be used to evaluate the therapeutic benefits or toxicities of a drug compound. Micro-organ devices as disclosed herein can address the need for in vitro micro-organs that substantially replicate in vivo structure and function.

The micro-organ devices (MODs) in accordance with embodiments of the invention may be produced by direct bioprinting of specific cells, human or animal, to form micro-organs in micro-chambers of microchips. Bioprinting processes are controllable and can produce reproducible micro-organs that also mimic the in vivo functions more closely. The process of bioprinting may use a technology known as "Computer Aided Tissue Engineering" or "CATE" for short, such as the technology developed at a laboratory located at Drexel University in Philadelphia, Pa. CATE is used in the design, simulation, and fabrication of cells/tissue to construct micro-organs. As will be discussed in more detail below, a CATE system integrates computer-aided design (CAD) technologies and modern design and manufacturing in bioengineering and biomedicine. The CAFE system employs a biopolymer deposition system that is capable of extruding biopolymer solutions and living cells for freeform construction of three-dimensional tissue scaffolds. The deposition process is biocompatible and occurs at room temperature and low pressures to reduce damage to cells. The CATE system is capable of, simultaneously with scaffold construction, depositing controlled amounts of cells, growth factors, or other bioactive compounds with precise spatial position to form complex cell-seeded three-dimensional tissue constructs. An example of a CATE system is given in Khalil et al., "*Multi-nozzle Deposition for Construction of 3D Biopolymer Tissue Scaffolds*," Rapid Prototyping Journal 2005, Vol. 11, No. 1: 9-17, which is hereby incorporated by reference. In accordance with other embodiments, the methods of fabricating a micro-organ device may also comprise forming microchips that include microfluidic channels and micro chambers for housing micro-organs.

Figure 1:
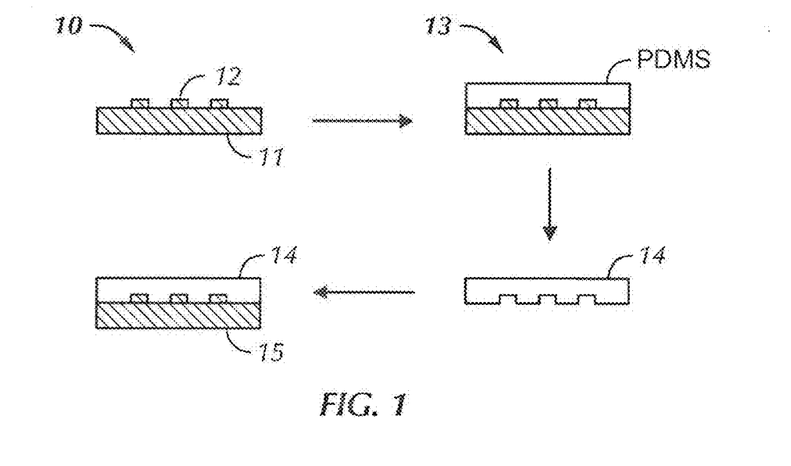
FIG. 1 shows a schematic series of processing steps illustrating a method for fabricating a microscale support or microchip for a micro-organ device in accordance with one embodiment of the invention.

Referring now to FIG. 1, an exemplary method that can be used to fabricate a microchip is illustrated in a series of steps. As shown in FIG. 1, a master 10 for making at least one microchip comprises a design pattern 12 on a silicon wafer 11. The master 10 may be fabricated using techniques that are adapted from lithographic techniques commonly used in integrated circuit (IC) chip manufacturing. Examples of using the lithographic techniques to fabricate tissue/organ devices can be found in U.S. Pat. No. 7,288,405, which is hereby incorporated by reference. The design pattern 12, for example, may include fluid communication channels or conduits and tissue chambers for forming a micro-organ device. A suitable polymer reagent is then poured onto the master 10 and allowed to cure, as shown in 13, to form a replica of the master 10. Any suitable polymer reagents may be used for making the replica. One suitable example includes a class of compounds generally referred to as polydimethyl siloxanes (PDMS). Other suitable materials may include rubber, polymers, plastic, elastomers, and silicone materials (such as Formulations RTV 108, RTV 615 or RTV 118 available from General Electric, New York, N.Y.).

As recognized by the skilled artisan, PDMS is a flexible elastomeric polymer that is an excellent material for fabrication of a microfluidic device. For instance, see McDonald et al., "*Fabrication of microfluidic systems in poly(dimethylsiloxane)*," Electrophoresis 2000, 21(1), pp. 27-40. Various PDMS are commercially available, including Sylgard® 184 from Dow Corning. Sylgard is a two-part resin system containing vinyl groups (part A) and hydrosiloxane groups (part B). Mixing of the two resins under appropriate conditions (e.g., by heating at a temperature of 65° C. or higher for 2 hours) leads to crosslinking (or curing), as illustrated below:

Once the polymer cures, the flexible replica 14 can be peeled off the master, leaving the master ready to produce another replica. The replica 14 has a pattern complementary to the design pattern 12. Once the replica 14 is peeled from the mold, it is ready for assembly to build a micro-organ device. The replica may be cut to proper size with a standard surgical blade, and access holes may be punched, if needed, for tubing and other conduits to provide access to the micro-organ device. For tubing inputs, a needle hole slightly smaller than the outer diameter of the tubing may be drilled so that adequate sealing can be achieved.

Another useful property of PDMS is that its surface can be chemically modified in order to obtain the interfacial properties of interest. See, Makamba et al., "*Surface modification of poly(dimethylsiloxane) microchannels*," Electrophoresis 2003, 24(21), 3607-19. One suitable method to covalently functionalize PDMS is to expose it to an oxygen plasma, whereby the surface of Si—$CH_3$ groups along the PDMS backbone are transformed into Si—OH groups by the reactive oxygen species in the plasma. For example, the PDMS surface may be exposed to $O_2$ plasma (100 mW radiofrequency, 1% $O_2$) for 30 seconds to convert the surface methyl silane groups into silanol groups.

Figure 2:
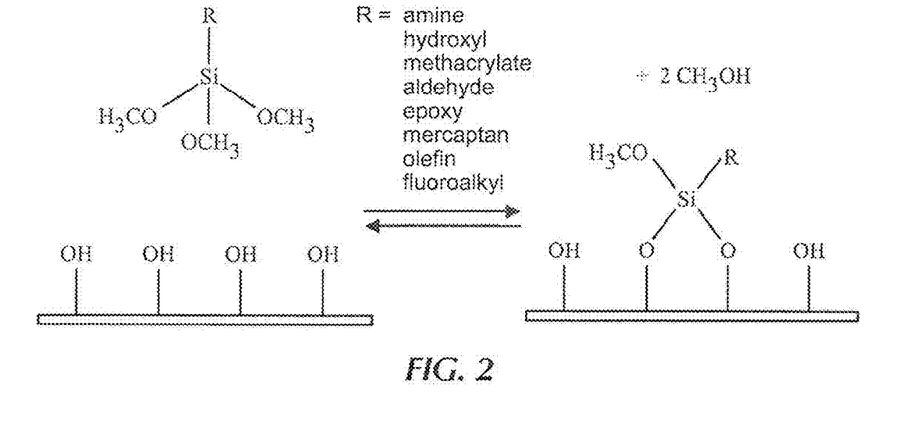
FIG. 2 illustrates possible chemical modification reactions of silanol groups on a polydimethyl siloxane (PDMS) microchip.

These silanol surfaces can then be transformed with other alkoxysiloxanes to yield many different chemistries, some of which are illustrated in FIG. 2, to facilitate further modification or reaction on the replica. The modified PDMS surface, which now has modified siloxane groups, can be reacted and bonded with another object 15 that contains silanol groups, such as a glass surface, another PDMS, or the like. In one embodiment, bonding of the PDMS microchip to a PDMS-coated glass slide acting as a substrate is accomplished by covering both contact surfaces with titanium tetra(isopropoxide). Alternatively, the original PDMS replica 14 from the polymerization reaction shown above (which contains methyl siloxane groups) can be reacted directly with silanol groups from the other object 15. With either approach, a microchip comprising at least one microfluidic channel and at least one micro-chamber can be readily prepared and provided.

Figure 3:
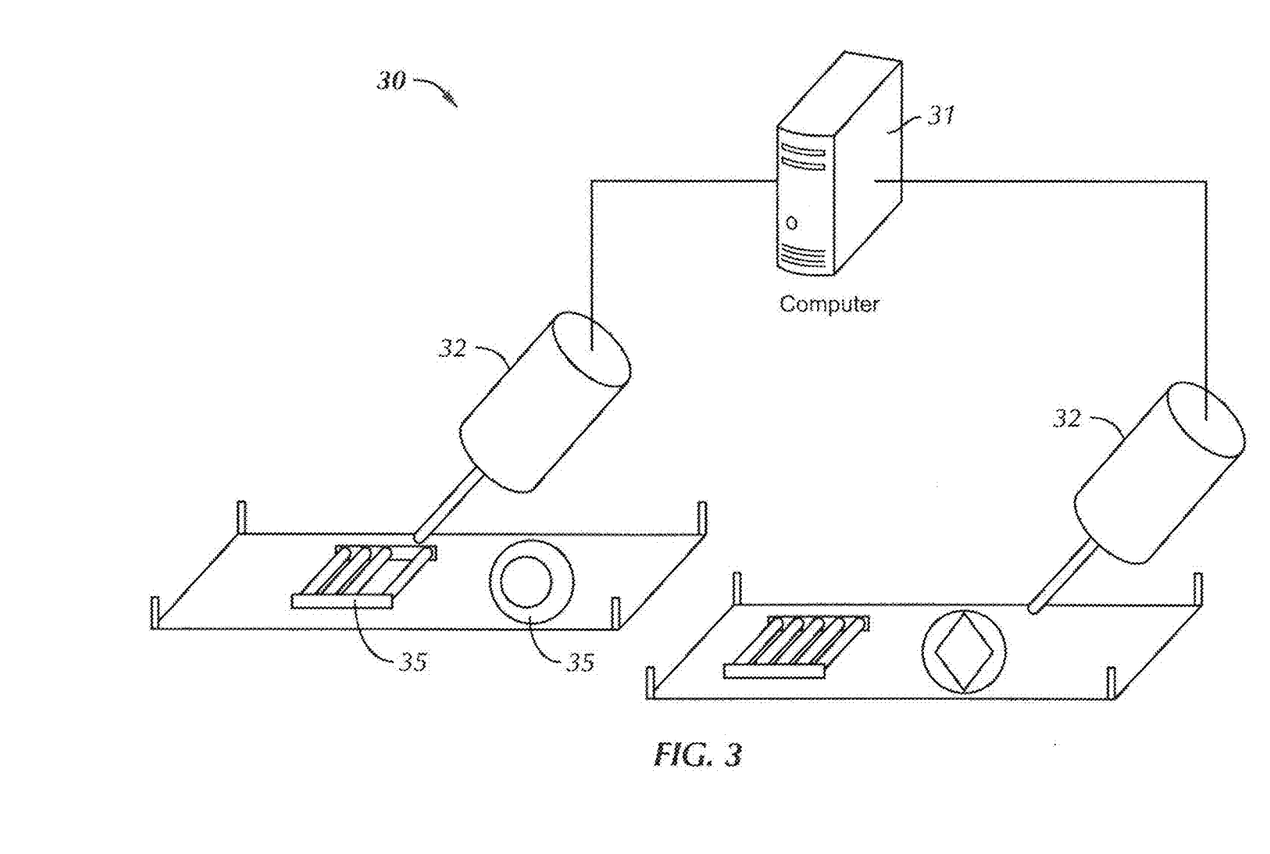
FIG. 3 shows a schematic series of processing steps illustrating a computer-aided tissue engineering system that can be used to bioprint micro-organ devices in accordance with one embodiment of the invention.

In accordance with embodiments of the invention, the cells or tissue of interest for mimicking organs may be fabricated or printed for placement into at least one micro-chamber of a fabricated microchip by a bioprinting system such as a computer-aided tissue engineering (CATE) system 30 of FIG. 3. System 30 enables computer-aided three-dimensional (3-D) printing of biopolymer scaffolds and cell-encapsulated scaffolds. The technique for fabrication employs solid freeform fabrication (SFF), which are computerized fabrication techniques that can rapidly produce highly complex three-dimensional objects using data from CAD systems and from computer medical imaging equipment such as Magnetic Resonance Imaging (MRI) and Computed Tomography (CT) scans. The fabricated three-dimensional structures are built by reducing CAD designs of particular interest into a group of sliced two-dimensional layers, to where the prototyping material is deposited to build the structure in a layer-by-layer process.

System 30 comprises a computer 31 for controlling the placement and movement of one or more syringes 32. The computer 31 includes at least one central processing unit (CPU) for processing a set of program instructions and memory for storing at least one CATE program comprising a set of program instructions. The at least one CATE program is written so as to direct a path of movement and placement of a robotic-arm to deposit alginate or a cell/alginate mixture from a syringe onto a substrate in accordance with a particular design or pattern. A CATE program typically includes computer-aided design/engineering/manufacturing (CAD/CAE/CAM) software. The CATE system 30 may comprise a precision deposition system, which includes the syringes 32 shown in FIG. 3, along with a robotic arm (not shown) for maneuvering the syringes as they "print" onto a particular surface. Cells for bioprinting are suspended in a solution containing extra-cellular matrix (e.g., collagens) and/or scaffold materials (e.g. alginates) and loaded in the syringes 32 for bioprinting the micro-organs 35. In one embodiment, a 1.5% (w/v) alginate is cross-linked with a calcium chloride solution and then injected onto the surface by syringe 32.

The CATE system can easily print three-dimensional cell-encapsulated scaffolds on the order of centimeters. Smaller dimensions are more of a challenge. In some embodiments, a strut width between ~125-500 microns (um) was accomplished. The strut width can be altered by changing the outlet gauge of the syringe and the flow pressure of the solution.

Figure 4A:
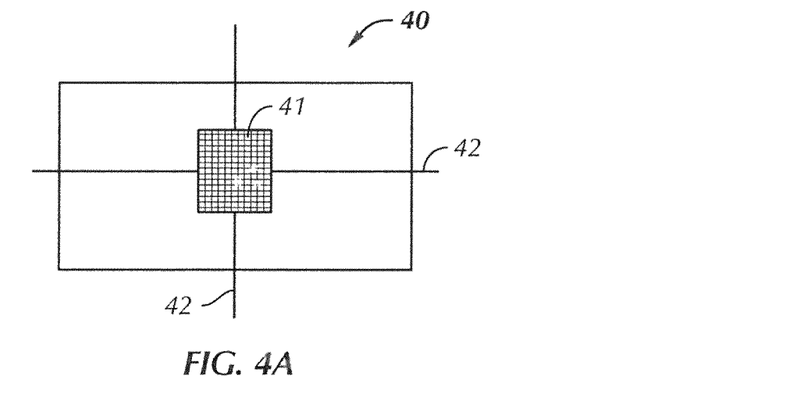
FIGS. 4A-4C show three micro-organ devices each having different configurations of organ arrays and microfluidic channels in accordance with embodiments of the invention.
Figure 4B:
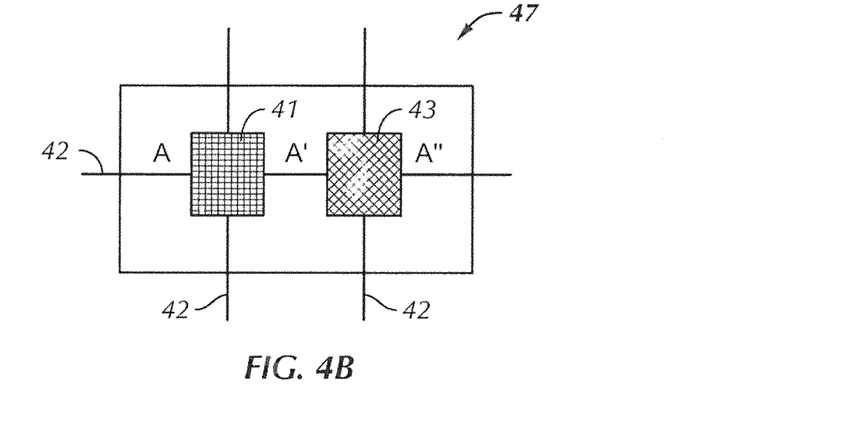
Figure 4C:
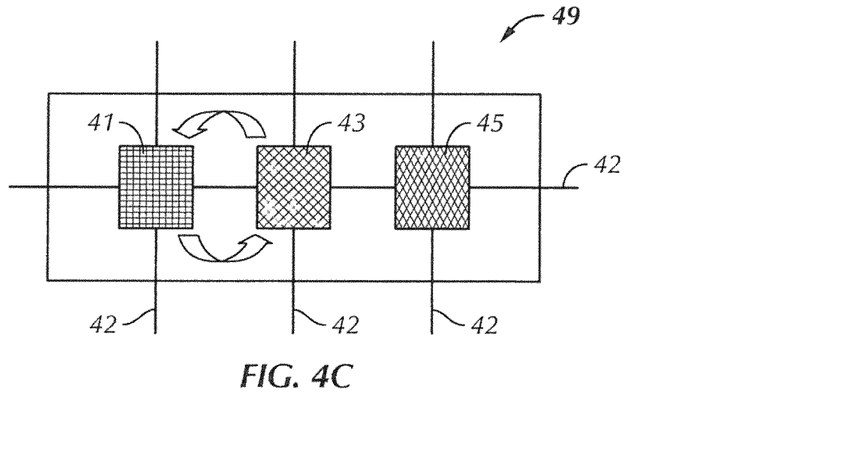

Using the methods and systems described herein and illustrated in FIGS. 1-3, or a variation thereof, microscale supports or microchips are combined with a bioprinting system to fabricate micro-organ devices in accordance with another embodiment. After loading the cells in the micro-chambers (using the bioprinting process), micro-organ devices (MOD) are obtained. These MODs may have various configurations of micro-chambers for housing micro-organs interconnected by microfluidic channels to simulate the fluid communications between these organs in vivo. FIGS. 4A-4C illustrate three embodiments that exemplify such configurations.

FIG. 4A shows a micro-organ device 40 that comprises a single micro-organ 41 in communication with two micro-channels or conduits 42. Device 40 is useful for assessing the effects (beneficial or toxic) on a particular organ and/or the mechanisms underlying these effects. For example, the micro-organ 41 may be a liver or kidney, and the device may be used to assess the toxicity of various drugs to the liver or kidney. Further, device 40 may be used to study metabolism of a drug by a particular organ, such as the liver. The liver has critical functions in various biological pathways involving xenobiotics, such as drugs. The functions of a liver may include converting a pro-drug into an active drug, converting a drug into a metabolite that may be more active or less active, converting a toxic compound into a soluble form for excretion (detoxification), etc.

Therefore, a micro-organ device having a micro-liver will allow a scientist or researcher to use such a device to study reactions of a biologic or other substance without resorting to animal or human tests. In such assays, a drug or test compound may be supplied in a solution from one end of a micro-channel 42. The capillary effect and gravity may be used to draw the solution into the micro-chamber, where the micro-liver 41 is located, and out the other end of the micro-channel 42. If necessary, pumps, pressure or vacuum may also be used to circulate the fluids in the microfluidic channels. The metabolites or modified drugs collected from the outlet may be analyzed to elucidate the liver metabolism pathways or to study the enzyme activities. In addition, the modified drugs may be used to test on a target micro-organ, or the like.

FIG. 4B shows an alternate micro-organ device 47 comprising two micro-organs 41 and 43. The micro-organ device 47 further comprises several micro-channels or conduits 42 for flowing solutions containing compounds to be tested. Device 47 is suitable for studying the interactions between the micro-organs 41 and 43 or the impacts of the presence of one micro-organ (e.g., 41) on the other (e.g., 43) when a drug is administered.

For example, the micro-organ 41 may be a micro-liver, while the micro-organ 43 may be the intended target for the drug (e.g., bone). When a drug A is passed through the micro-organ 41 (e.g., liver), it may be converted into a metabolite A', which may be more active or less active than the original drug. The metabolite A' then acts on the target organ (e.g., the micro-organ 43). After acting on the target organ, the metabolite A' may be further metabolized to a new metabolite A". With such a device, pharmacokinetic and pharmacodynamic studies would be performed under conditions more closely related to in vivo conditions than using a cell culture or a single organ device.

A micro-organ device may comprise any number of micro-organs. With a proper design of micro-chambers and interconnecting micro-channels, the various interactions between the organs in a human may be replicated or at least mimicked. FIG. 4C illustrates another embodiment, which shows a micro-organ device 49 that comprises three micro-organs 41, 43, and 45. The three micro-organs 41, 43, and 45 are interconnected via micro-channels or conduits 42. Two curvy arrows in this figure signify that crosstalk exists between micro-organs 41 and 43. The communication between the micro-organ 41 and 43 may be via one or more microfluidic channels. The crosstalk may be mediated by the modified compound (i.e., metabolite) after conversion by a micro-organ. Alternatively, the crosstalk may be mediated by paracrine factors, hormones, or other factors that are secreted by the cells of the micro-organs in response to a stimulus, e.g., the drug or a metabolite of the drug.

Note that the examples shown in FIGS. 4A-4C are illustrative only. One of ordinary skill in the art, now having benefit of this detailed description, would appreciate that embodiments of the invention are not so limited and that modifications or variations from those shown are possible without departing from the scope of the invention. For example, the micro-channels in these illustrations are shown to have open ends. Some of these open ends may be interconnected to form loops or circuits. Similarly, the multiple micro-organs shown in FIG. 4C are arranged (and connected by microfluidic channels) in series (i.e., aligned sequentially). Other embodiments may comprise multiple micro-organs that are connected by microfluidic channels in "parallel" or in a web.

The microfluidic channels illustrated in the devices of FIGS. 4A-4C may be on the order of tens to hundreds of micrometers (μm) wide, while the micro-chambers that house the micro-organs may have a dimension as large as 1 cm or more. If the micro-organ were a solid mass of a millimeter (mm) or centimeter (cm) in size, the cells in the interior of the micro-organ would not be able to exchange efficiently with the media in the microfluidic channels. In general, to ensure effective diffusion exchange, cells are preferably not more than 500 μm away from the microfluidic channels. In order to ensure efficient diffusion exchanges, a micro-organ in accordance with the embodiments may comprise substructures, at least one dimension of which is preferably no larger than 1 millimeter (mm), more preferably less than 500 μm. Such micro-organs may be prepared according to the structural embodiments of FIGS. 5A-8, using the CATE system shown in FIG. 3.

Figure 5A:
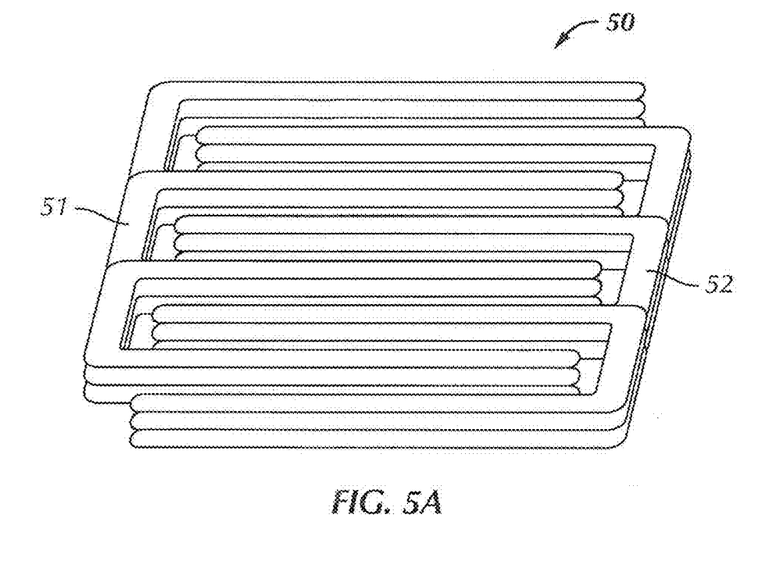
FIGS. 5A and 5B show perspective views along the top and side, respectively, of a section of a micro-organ, illustrating the substructures produced with bioprinting, in accordance with one embodiment.
Figure 5B:
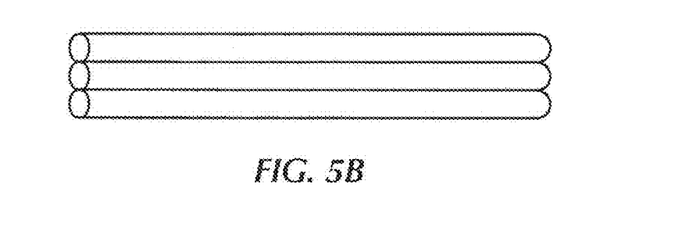

Referring now to FIG. 5A, a perspective top view of one structural embodiment that may be bioprinted is shown so as to construct a three-dimensional tissue model of a micro-organ. In particular, two substructures 51 and 52 of a micro-organ 50 are shown to have been fabricated (bioprinted) in an interdigitated configuration having microscale spacing between one another. The spacing between the two sub-structures 51 and 52 are designed to form the microfluidic channel 53 for the flow or circulation of media to nourish cells or tissue. FIG. 5B shows a side view of the substructures of FIG. 5A, further illustrating the 3-D structure of the tissue model comprising multiple layers or "struts" of scaffolding. Although only three layers of the substructures are shown in this illustration, a micro-organ may comprise more or less layers in other embodiments, as will be discussed with reference to FIGS. 6-8. In this particular example, each layer is about 200 μm thick, and the spacing between the substructures forming the channel 53 is about 20 μm. This particular microscale thickness and microscale spacing enables cells at the interior of the micro-organ to efficiently exchange with the media (by diffusion) in the micro-channels.

The interdigitated substructures and the multi-layer stacking may be bioprinted using the CATE system shown in FIG. 3. When bioprinting is used, cells of the micro-organ are suspended in a solution containing one or more extra-cellular matrix or scaffold materials. The solution is put in a syringe that is controlled by a computer for "printing" the micro-organ onto a surface, such as a microchip, according to a particular design. The printing process may be performed one layer at a time until the desired number of layers of the substructure is achieved.

Figure 6:
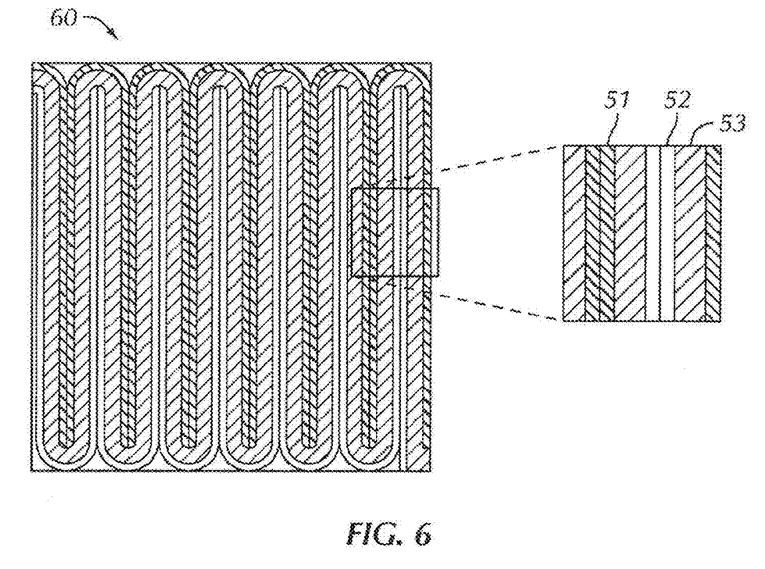
FIG. 6 is a two-dimensional cross sectional view of a three-dimensional micro-organ in accordance with one embodiment of the invention.

The interdigitated configuration of the substructures 51 and 52 and the microscale spacing between them that forms the microfluidic channels 53 are also shown in a top view in FIG. 6. This top view shows a section of an entire micro-organ 60 comprising repeated layers (interdigitated folds) of substructures 51, 52, and the microfluidic channel 53 to achieve a particular overall dimension of interest (e.g., 1 cm).

Figure 7:
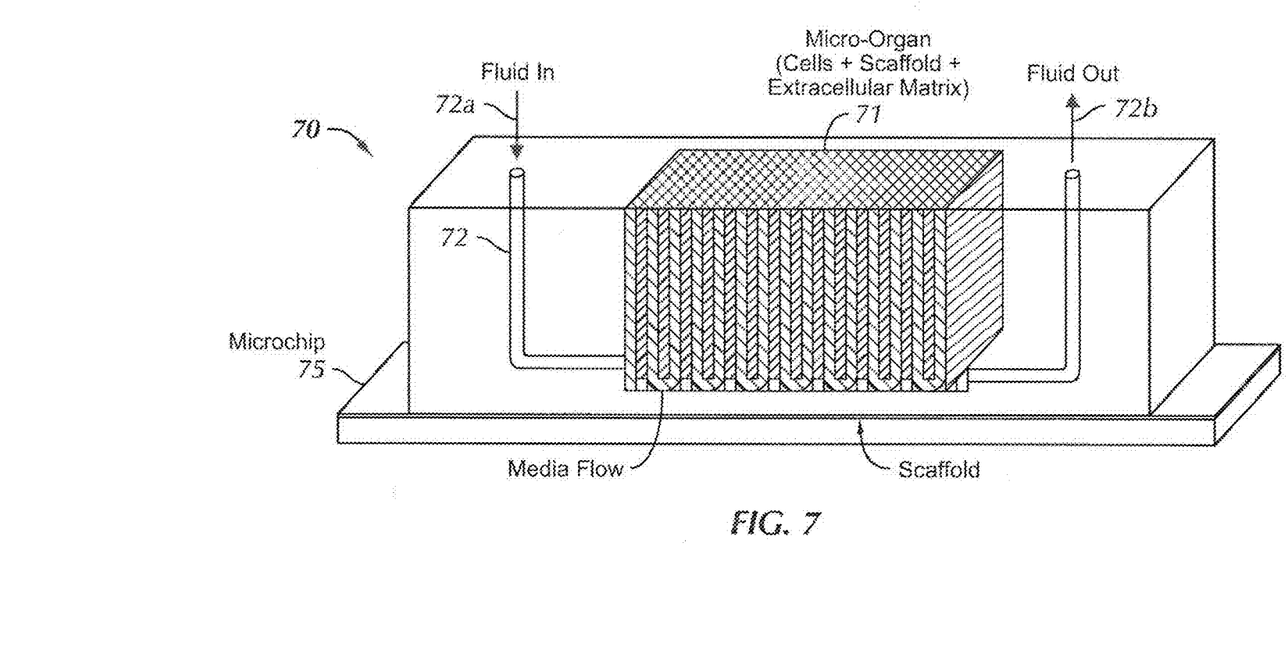
FIG. 7 is a perspective view of a three-dimensional micro-organ device in accordance with one embodiment of the invention.

The two-dimensional (2D) top view shown in FIG. 6 represents a layer (section) of a 3D) micro-organ. FIG. 7 shows a perspective view of a 3D micro-organ 71 that comprises a plurality of the 2D sections shown in FIG. 6. FIG. 7 shows that the 3D micro-organ 71 is disposed in a micro-chamber of a micro-organ device (MOD) 70. The micro-organ device (MOD) 70 also comprises a microfluidic channel or conduit 72 with an inlet 72a and an outlet 72b. As noted above, the MOD 70 may be made of any suitable materials, such as PDMS. The MOD 70 is shown to be supported on a substrate or chip 75, which may be a silicon wafer, glass, glass coated with PDMS, or plastic and have a dimension on the order of one to several centimeters.

Figure 8:
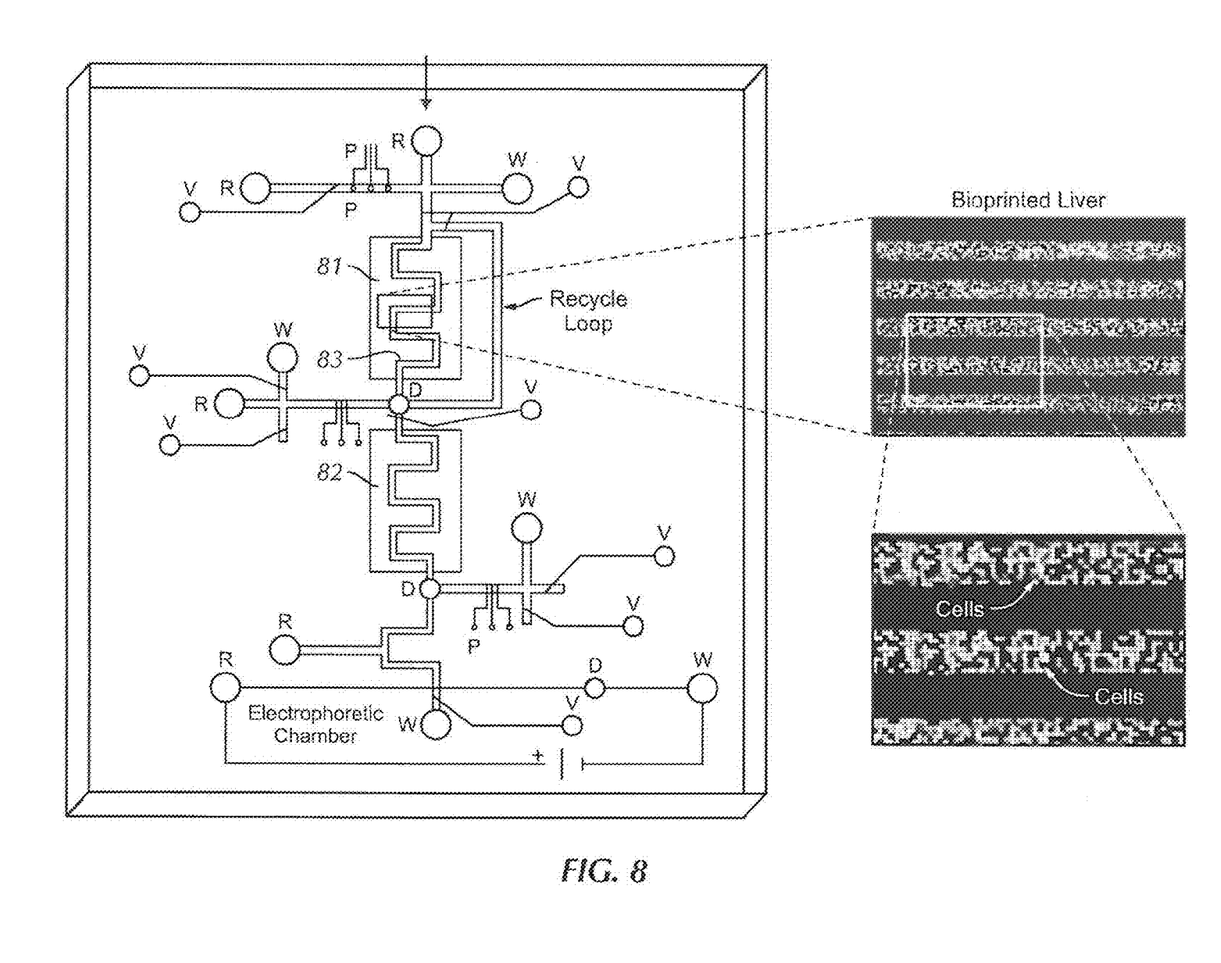
FIG. 8 shows a schematic diagram of a system comprising two micro organs illustrating various microfluidic channels and interconnections in accordance with another embodiment.

As shown in FIGS. 4B and 4C, a micro-organ device (MOD) of the invention may include more than one micro-organ, which may be operatively interconnected to one another by one or more microfluidic channels. FIG. 8 shows a system 80 in accordance with one embodiment of the invention that comprises two micro-organs 81, 82 connected by a network of microfluidic channels 83. The network of microfluidic channels 83 is shown to include various valves (denoted by the reference character V), reservoirs (R), pumps (P), and detectors (D).

In the example shown in FIG. 8, the chip footprint may be in the range of 1-5 cm×1-5 cm. The fluidic channels may be about 25-50 µm deep and about 100-350 µm wide. The fluidic channels in the electrophoresis chamber or section may be smaller, e.g., about 50 µm wide. The valves (V) may be controlled by pneumatic control lines, which serve to actuate the valves for controlling fluid flow and fluid pumping. The pneumatic control lines may be 10 µm deep and 200 µm wide, for example. Note that these dimensions are for illustration of this particular example. One of ordinary skill in the art, now having benefit of this description, would appreciate that a MOD in accordance with other embodiments may also be prepared in other sizes and dimensions.

The pumps shown in FIG. 8 may be peristaltic pumps or syringe pumps. The detector may be any suitable detector (optical, UV, fluorescence, IR, laser, etc.) for detecting or assessing drug conversion or metabolite analysis. The system shown in FIG. 8 also includes an electrophoresis separation and detection section, which may be used to analyze any metabolites or converted drugs.

The methods for bioprinting of cells in accordance with embodiments of the invention do not adversely impact the viability of the cells. In one example, using mouse hepatocytes (ATCC, CRL-2254) encapsulated in alginate hydrogels, it was found that the resultant micro-organ retained 79% viable cells. A micro-organ of liver cells thus prepared was found to produce a higher amount of urea than the same number of hepatocytes cultured on tissue culture plastic, suggesting that the cells in the MOD are healthier.

Figure 9:
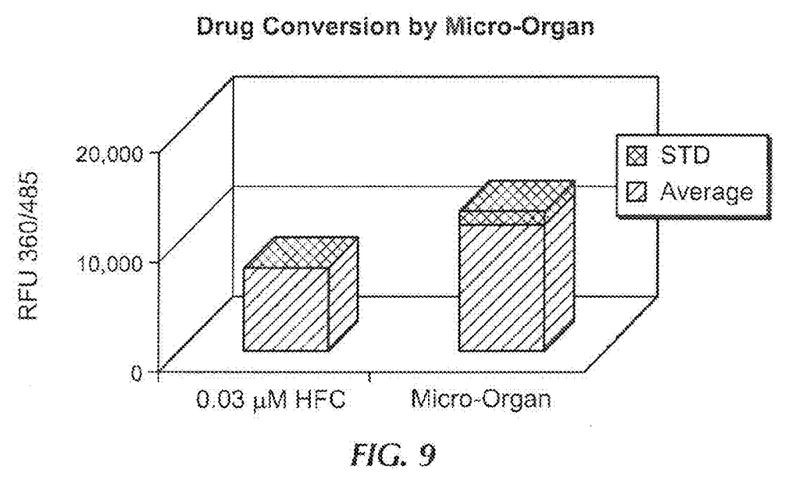
FIG. 9 represents a chart of results from an activity assay using a liver micro-organ device in accordance with one embodiment.

More importantly, micro-organ devices constructed in accordance with these methods are found to be able to perform functions that mimic, or are similar to, the in vivo functions of the corresponding organ. For example, FIG. 9 is a chart of results from an experiment concerning the conversion of 7-ethoxy-4-trifluoromethylcoumarin (EFC) to 7-hydroxy-4-trifluoromethylcoumarin (HFC) by a liver micro-organ device in accordance with one embodiment of the invention. EFC is converted to HFC by liver cytochromes P450 (P450s). Liver cytochrome P450 enzymes are involved in drug metabolism. EFC has weak or no fluorescence, while HFC has strong fluorescence. Therefore, this system provides a convenient assay for the drug metabolizing enzymes in the liver. Liver MODs in accordance with an exemplary embodiment are found to convert EFEC to HFC at rates ranging from 1 to 10 picomoles/hr/$10^4$ cells. Results shown in FIG. 9 indicate the MODs can have functions like those of its corresponding in vivo organs. Thus, MODs can be used to mimic such organs for the study of drug metabolism or other pharmacokinetic applications.

In particular, at least one embodiment of the micro-organ-device (MOD) may be designed to mimic the complex in vivo microenvironment of human or animal cells and tissue, including proper inter-communications between different organs, by constructing a three-dimensional tissue model to be housed within a microchip that replicates the in vivo micro-organ structure, extra-cellular matrix composition and architecture, and the in vivo fluid flow. One or more micro-organs may be created by suspending human or animal mammalian cells in a specific soluble extra-cellular matrix (ECM) and scaffold and printing three-dimensional micro-organs with a computer aided tissue engineering (CATE) system. The micro-organs may be directly printed and arrayed as single or multi-organs on at least one microchip or microfabricated microfluidic device. The microchip houses the micro-organs to form a micro-organ device. Fluids are then circulated through the micro-organs to maintain viability and to deliver specific soluble factors and molecules. A system, such as the system 80 of FIG. 8, may be constructed to control and direct the perfusion of cell culture medium and specific soluble factors such as investigative drugs and chemicals using algorithms related to the law of mass conservation.

In one embodiment, system 80 may be constructed to control and direct perfusion by equations related to the conservation of mass. First, the rate of metabolism in the tissue analog (or MOD), represented by the variable $R_m$, is a product of the volume of in-flow to the tissue analog from which the drug would be entirely removed in unit time, represented by the variable CL, and the drug concentration entering the tissue analog, as represented by the variable $C_1$. This relation may be denoted by the equation:

$$R_m = CL * C_1.$$

The tissue analog of this embodiment may be represented as comprising the following additional set of variables:
  Q=circulating rate of perfusate;
  $C_2$=drug concentration exiting tissue analog;
  R=constant rate of continuous infusion; and,
  D=total amount of drug in the medium.
Further, given that $$V_1 \frac{dC_1}{dt} = -QC_1 + QC_2 + R, \quad (1)$$

$$V_2 \frac{dC_2}{dt} = -QC_2 + QC_1 - CLC_1, \quad (2)$$

and that for initial conditions $$C_1\big|_{t=0} = \frac{D}{V_1}, C_2\big|_{t=0} = 0, R = 0,$$

CL may be obtained from the following relation:

$$\frac{A}{\alpha} + \frac{B}{\beta} = \frac{D}{CL}, \text{ or } CL = \frac{D\alpha\beta}{\beta A + \alpha B}. \quad (3)$$

Thus, CL is dependent on the amount of drug in the medium (D), which in turn relates to the drug concentration entering the tissue analog ($C_1$), the variables α, β, which relate to the slope of a graph dependent on cell density and cell type (i.e., biomaterial properties), and the variables A, B, which are intercept values of a graph that is dependent on Q, the flow rate of perfusate (medium+drug) and $V_2$, the flow volume of constructed microchannel (length times cross sectional area).

Bioprinting of cells, ECM, and scaffolding with a CATE system, directly onto the microfluidic microchip for in vivo-like three-dimensional architectures and arrays, provides excellent reproducibility and quality control. With this method, it becomes possible to design and test various drugs in a more in vivo-like platform that mimics proper inter-communications between different organs. FIGS. 10A-10E illustrate some configurations that are exemplary platforms. For instance, the embodiment shown in FIG. 10A comprises a single micro-organ. This embodiment would be useful for studying the effects of drugs on the target organ, biological functions of the target organ, or to use the target organ to convert the drugs to new metabolites, such as the conversion charted in FIG. 9.

Figure 10A:
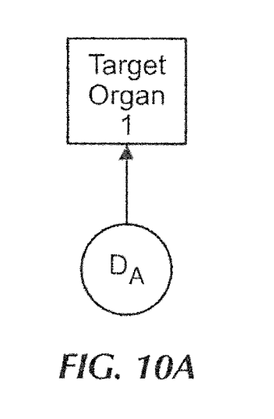
FIGS. 10A-10E show examples of various configurations and arrays that may be produced for pharmacokinetic studies in accordance with another embodiment of the invention.
Figure 10B:
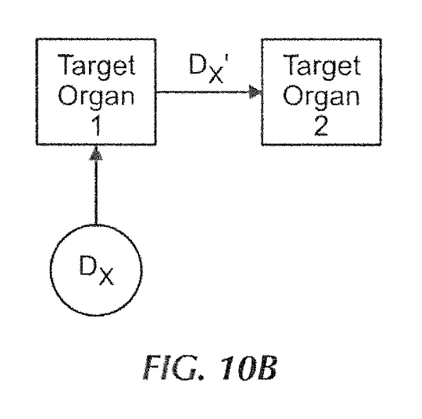

FIG. 10B shows an embodiment comprising two target micro organs. The first target organ (e.g., liver) converts a drug ($D_X$) into a new compound ($D_X'$) that then acts on the second target organ. This embodiment can be used to study the conversion of a drug to a new metabolite and its effect on a target organ.

Figure 10C:
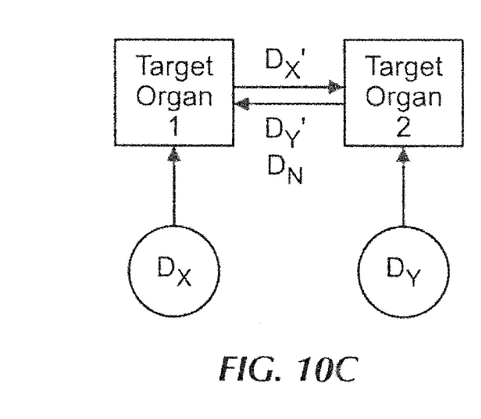

FIG. 10C shows another embodiment comprising two target micro organs in which the two organs interact with each other. Thus, a drug ($D_X$) converted by the first target organ to a new compound ($D_X'$) acts on the second target organ, while another drug or compound ($D_Y$), converted by the second target organ to a new metabolite ($D_Y'$), can have an effect on the first target organ.

Figure 10D:
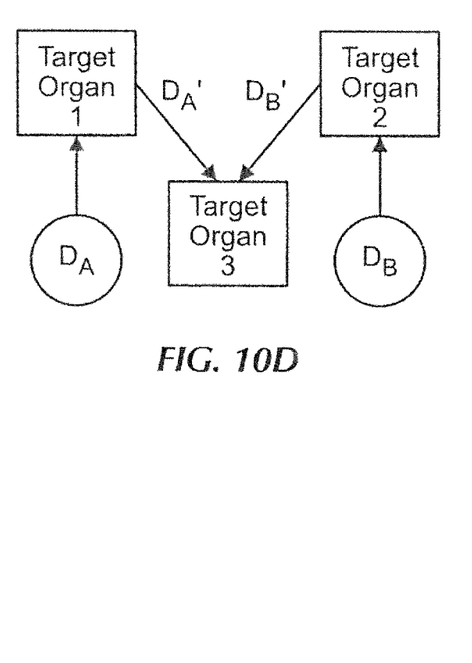

FIG. 10D shows an embodiment of an MOD comprising two micro organs that independently regulate a third organ. These two organs may convert drugs ($D_A$, $D_B$) to metabolites ($D_A'$, $D_B'$) that affect a third organ. Alternatively, these two organs may secrete biological effectors ($D_A'$, $D_3'$) in response to the stimuli of drugs ($D_A$, $D_B$) that act on a third organ.

Figure 10E:
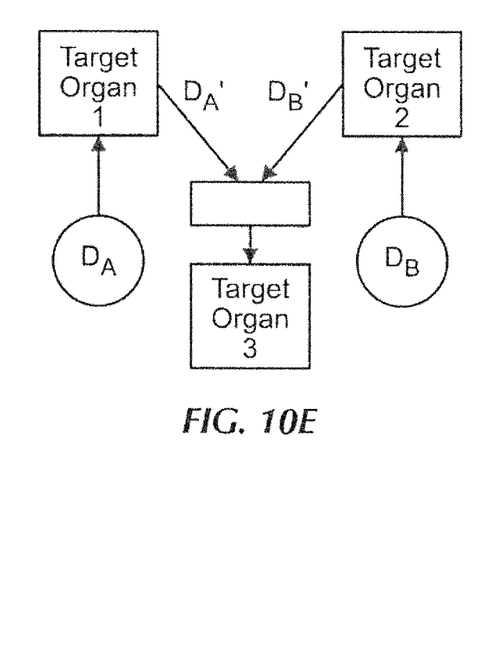

FIG. 10E shows an embodiment of an MOD comprising two organs that may jointly regulate a third organ. In this case, the metabolites or biological effectors ($D_A'$, $D_B'$) produced by the first two organs may need to be combined (e.g., dimmer formation) in circulation before they can act on the third organ. Alternatively, the two metabolites or biological effectors ($D_A'$, $D_B'$) may act on an intermediate organ, which then produces a signal to regulate the third target organ.

The various embodiments shown in FIGS. 10A-10E are for illustration only. One of ordinary skill in the art, now having benefit of this description, would appreciate that various other configurations may be made with MODs to suit the purposes of his studies.

Advantages of the methods disclosed in accordance with exemplary embodiments of the invention include biopatterning and bioprinting of cells, extracellular matrices, and scaffolding directly on microfluidic microchips. The methods also minimize variations in local seeding densities and selection pressures that favor more aggressive cells. Direct bioprinting also enables precise and simultaneous coupling of multiple microfluidic channels on one microchip with those on another microchip. The methods allow control of volumetric and quantitative accuracy for specific applications, such as pharmacodynamics, pharmacokinetics, and toxicity studies. The methods also enable reproduction of in vivo circulation profiles within and between micro-organs. MODs in accordance with embodiments of the invention can be automated, require minimal footprints and power requirements, use micro-volumes of fluids and generate minimal amounts of waste, and can provide high throughput and parallel analyses on the same microchip.

Micro-organ devices fabricated in accordance with exemplary embodiments of the invention should also require minimal resources for an investigation of toxicology and pharmacological effects, in that the MOD would mimic an in vivo situation without use of human or animals. Results from an MOD system should have high extrapolation to a similar animal or human study. Thus, the MODs may be used both in space and on Earth as a drug screening system with human cell micro-organs to either supplement the results of, or reduce the number of, animal studies. Such an alternative assay platform would likely result in a greater proportion of candidate drugs to "fail early" prior to clinical trials than the current approach using animal studies, potentially reducing costs and maximizing resources and later success by enabling the accurate selection of a smaller number of candidates for in vivo drug metabolism and drug target validation. Thus, accurate predictive models comprising MODs should also increase the likelihood of successful clinical trials.

Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims. In the claims, means-plus-function and step-plus-function clauses are intended to cover the structures or acts described herein as performing the recited function and not only structural equivalents, but also equivalent structures. Thus, while a nail and a screw may not be structural equivalents in that a nail employs a cylindrical surface to secure wooden parts together, whereas a screw employs a helical surface, in the environment of fastening wooden parts, a nail and a screw may be equivalent structures.

What is claimed is:

1. A micro-organ device, comprising:
   at least one micro-chamber for housing a micro-organ; and
   at least one microfluidic channel connected to the micro-chamber,
   wherein the micro-organ comprises cells arranged in a configuration that includes microscale spacing between portions of the cells to facilitate diffusion exchange between the cells and a medium supplied from the at least one microfluidic channel, wherein the micro-organ device is prepared by process comprising:
      providing a microscale support comprising the at least one microfluidic channel and the at least one micro-chamber for housing a micro-organ;

bonding the microscale support to a substrate by covering the contact surfaces of each with titanium tetra (isopropoxide); and printing the micro-organ on the microscale support using a cell suspension in a syringe controlled by a computer-aided tissue engineering system, wherein the cell suspension comprises the cells suspended in a solution containing a material that functions as a three-dimensional scaffold, and wherein the printing is performed with the computer-aided tissue engineering system according to a particular pattern.

2. The micro-organ device of claim 1, wherein the cells are liver cells.

3. The micro-organ device of claim 1, wherein the at least one micro-chamber for housing a micro-organ comprises two micro-chambers housing two different micro-organs.

4. The micro-organ device of claim 3, wherein one of the two different micro-organs comprises liver cells.

5. The micro-organ device of claim 1, wherein the configuration of the micro-organ comprises a pair of interdigitated substructures.

* * * * *